US009794996B2

United States Patent
Soler et al.

(10) Patent No.: US 9,794,996 B2
(45) Date of Patent: *Oct. 17, 2017

(54) SYSTEM AND METHODS FOR OPERATING A LIGHTING DEVICE

(71) Applicant: Lighting Science Group Corporation, Cocoa Beach, FL (US)

(72) Inventors: Robert R. Soler, San Marcos, CA (US); Fredric S. Maxik, Cocoa Beach, FL (US); David E. Bartine, Cocoa, FL (US); Mark Andrew Oostdyk, Cape Canaveral, FL (US); Matthew Regan, Melbourne, FL (US)

(73) Assignee: Lighting Science Group Corporation, Cocoa Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/370,802

(22) Filed: Dec. 6, 2016

(65) Prior Publication Data

US 2017/0086273 A1 Mar. 23, 2017

Related U.S. Application Data

(63) Continuation of application No. 14/573,922, filed on Dec. 17, 2014, now Pat. No. 9,532,423, which is a (Continued)

(51) Int. Cl.
*H05B 37/02* (2006.01)
*H05B 33/08* (2006.01)
(Continued)

(52) U.S. Cl.
CPC ......... *H05B 33/0845* (2013.01); *A61M 21/00* (2013.01); *A61M 21/02* (2013.01);
(Continued)

(58) Field of Classification Search
CPC ............ H05B 33/0845; H05B 33/0857; H05B 33/086; H05B 33/0863; H05B 33/0872; A61M 21/00; A61M 21/02
(Continued)

(56) References Cited

U.S. PATENT DOCUMENTS 7,759,854 B2 * 7/2010 Miller ................ H05B 33/0812
313/498
8,723,450 B2 * 5/2014 Hatley ................ H05B 33/086
315/312

(Continued)

FOREIGN PATENT DOCUMENTS

WO 2006039789 A1 4/2006
WO 2008146219 A1 12/2008
WO 2010122446 A1 10/2010

OTHER PUBLICATIONS

Extended European Search Report dated Nov. 3, 2016 filed in related European Application No. 14774608.5 (7 pages).

*Primary Examiner* — Jason M Crawford
(74) *Attorney, Agent, or Firm* — Mark Malek; Daniel Pierron; Widerman Malek PL

(57) ABSTRACT

A lighting device may include a light source, a control circuit, and a communication device positioned in communication with the control circuit. The communication device may be configured to receive a transmission from a user device, and the transmission may include a data structure. The data structure may include a show packet and an event packet. The show packet may include an ID string and information regarding a number of event packets associated with the data structure, and the event packet may include information regarding a lighting spectrum, a fade type, a fade duration, and a hold duration. The control circuit may be configured to operate the light source to emit light transitioning from a present light emission having a present
(Continued)

spectral power distribution to a light emission having spectral power distribution indicated by the lighting spectrum according to the fade type and fade duration.

21 Claims, 8 Drawing Sheets

Related U.S. Application Data continuation-in-part of application No. 14/315,660, filed on Jun. 26, 2014, now Pat. No. 9,024,536, which is a continuation-in-part of application No. 14/165,198, filed on Jan. 27, 2014, now Pat. No. 8,941,329, which is a continuation of application No. 13/311,300, filed on Dec. 5, 2011, now Pat. No. 8,686,641, said application No. 14/573,922 is a continuation-in-part of application No. 14/260,371, filed on Apr. 24, 2014, now Pat. No. 9,265,968, which is a continuation of application No. 13/803,825, filed on Mar. 14, 2013, now Pat. No. 8,743,023, which is a continuation-in-part of application No. 13/709,942, filed on Dec. 10, 2012, now Pat. No. 8,760,370, which is a continuation-in-part of application No. 13/234,371, filed on Sep. 16, 2011, now Pat. No. 8,465,167, and a continuation-in-part of application No. 13/107,928, filed on May 15, 2011, now Pat. No. 8,547,391, said application No. 13/803,825 is a continuation-in-part of application No. 13/652,207, filed on Oct. 15, 2012, now Pat. No. 8,643,276, which is a continuation of application No. 13/174,339, filed on Jun. 30, 2011, now Pat. No. 8,324,808, which is a continuation-in-part of application No. 12/842,887, filed on Jul. 23, 2010, now Pat. No. 8,253,336, said application No. 14/573,922 is a continuation-in-part of application No. 13/775,936, filed on Feb. 25, 2013, now abandoned, and a continuation of application No. 13/465,781, filed on May 7, 2012.

(60) Provisional application No. 61/923,924, filed on Jan. 6, 2014, provisional application No. 61/643,308, filed on May 6, 2012, provisional application No. 61/643,316, filed on May 6, 2012.

(51) Int. Cl.

| | | |
|---|---|---|
| *A61N 5/06* | (2006.01) | |
| *A61M 21/00* | (2006.01) | |
| *A61M 21/02* | (2006.01) | |
| *F21V 3/02* | (2006.01) | |
| *F21V 19/00* | (2006.01) | |
| *F21V 23/04* | (2006.01) | |
| *F21Y 101/00* | (2016.01) | |
| *F21K 9/23* | (2016.01) | |
| *F21Y 115/10* | (2016.01) | |
| *F21Y 113/13* | (2016.01) | |
| *F21V 29/74* | (2015.01) | |
| *F21K 9/238* | (2016.01) | |
| *F21K 9/232* | (2016.01) | |
| *F21K 9/235* | (2016.01) | |
| *F21K 9/237* | (2016.01) | |
| *F21V 23/00* | (2015.01) | |

(52) U.S. Cl.
CPC ......... *A61N 5/0618* (2013.01); *H05B 33/086* (2013.01); *H05B 33/0857* (2013.01); *H05B 33/0863* (2013.01); *H05B 33/0872* (2013.01); *H05B 37/0227* (2013.01); *H05B 37/0272* (2013.01); *H05B 37/0281* (2013.01); *A61M 2021/0044* (2013.01); *A61M 2021/0083* (2013.01); *A61N 2005/0652* (2013.01); *A61N 2005/0663* (2013.01); *F21K 9/23* (2016.08); *F21K 9/232* (2016.08); *F21K 9/235* (2016.08); *F21K 9/237* (2016.08); *F21K 9/238* (2016.08); *F21V 3/02* (2013.01); *F21V 19/0055* (2013.01); *F21V 23/005* (2013.01); *F21V 23/045* (2013.01); *F21V 29/74* (2015.01); *F21Y 2101/00* (2013.01); *F21Y 2113/13* (2016.08); *F21Y 2115/10* (2016.08)

(58) Field of Classification Search
USPC ................. 315/291–292, 294, 297, 307–308
See application file for complete search history.

(56) References Cited

U.S. PATENT DOCUMENTS

| | | | |
|---|---|---|---|
| 9,532,423 B2* | 12/2016 | Soler | A61N 5/0618 |
| 2007/0108846 A1 | 5/2007 | Ashdown | |
| 2008/0136334 A1* | 6/2008 | Robinson | H05B 37/0254 315/151 |
| 2010/0188022 A1 | 7/2010 | Gerlach et al. | |
| 2012/0019138 A1 | 1/2012 | Maxik et al. | |
| 2012/0112640 A1 | 5/2012 | Maxik et al. | |

* cited by examiner

SYSTEM AND METHODS FOR OPERATING A LIGHTING DEVICE

RELATED APPLICATIONS

This application is a continuation and claims priority under 35 U.S.C. §120 of U.S. patent application Ser. No. 14/573,922 titled Luminaire for Varying Biologically-Adjusted Illumination According To a User-Controllable Circadian pattern and Associated Systems and Methods filed Dec. 17, 2014 (hereinafter "the 922 application,", which in turn claimed priority under 35 U.S.C. §119(e) of U.S. Provisional Patent Application Ser. No. 81/923,924 titled Luminaire for Varying Biologically-Adjusted illumination According To a User-Controllable Circadian pattern and Associated Systems and Methods filed Jan. 8, 2014, and was a continuation-in-part of U.S. patent application Ser. No. 14/315,660 titled Tunable LED Lamp for Producing Biologically-Adjusted Light and Associated Methods filed Jun. 26, 2014 which, in turn, is a continuation-in-part of U.S. patent application Ser. No. 14/185,198 titled Tunable LED Lamp for Producing Biologically-Adjusted Light filed Jan. 27, 2014 (Ser. No. 13/311,300) which, in turn, is a continuation of U.S. Pat. No. 8,688,841 titled Tunable LED Lamp for Producing Biologically-Adjusted Light filed Dec. 5, 2011, the contents of each of which is incorporated herein by reference in its entirety except to the extent disclosure therein is inconsistent with disclosure herein.

Additionally, the '922 Application claimed priority under 35 U.S.C. §120 and was a continuation-in-part of U.S. patent application Ser. No. 14/260,371 titled System for Generating Non-Homogenous Biologically-Adjusted Light and Associated Methods filed Apr. 24, 2014 (Ser. No. 13/803,825), which is, in turn, a continuation of U.S. Pat. No. 8,743,023 titled System for Generating Non-Homogenous Biologically-Adjusted Light and Associated Methods filed Mar. 14, 2013 (Ser. No. 13/709,942), which is, in turn, a continuation-in-part of U.S. Pat. No. 8,760,370 titled System for Generating Non-Homogenous Light and Associated Methods filed Dec. 10, 2012, which, in turn, claims priority from U.S. Provisional Patent Application Serial No. 61/843,308 titled Tunable Light System and Associated Methods filed May 6,2012 (Ser. No. 13/234,371), U.S. Provisional Patent Application Ser. No. 61/643,316 titled Luminaire Having an Adaptable Light Source and Associated Methods filed May 6, 2012, and is a continuation-in-part of U.S. Pat. No. 8,465,167 titled Color Conversion Occlusion and Associated Methods filed Sep. 16, 2011 (Ser. No. 13/107,928) and is also a continuation-in-part of U.S. Pat. No. 8,547,391 titled High Efficacy Lighting Signal Converter and Associated Methods filed May 15, 2011, the content of each of which is incorporated by reference herein in their entireties, except to the extent disclosure therein is inconsistent with disclosure herein. Additionally, U.S. patent application Ser. No. 13/803,825 is a continuation-in-part of U.S. Pat. No. 8,643,276 titled LED Lamp for Producing Biologically-Corrected Light filed Oct. 15, 2012, (Ser. No. 13/174,339) which, in turn, is a continuation of U.S. Pat. No. 8,324,808 titled LED Lamp for Producing Biologically-Corrected Light filed Jun. 30,2011 (Ser. No. 12/842,887), which, in turn, is a continuation-in-part of U.S. Pat. No. 8,253,336 titled LED Lamp for Producing Biologically-Adjusted Light filed Jul. 23, 2010.

Furthermore, the '922 application was related to and claimed benefit under 35 U.S.C. §120 of U.S. patent application Ser. No. 13/775,936 titled Adaptive Light System and Associated Methods filed Feb. 25, 2013 and U.S. patent application Ser. No. 13/465,781 titled Dynamic Wavelength Adapting Device to Affect Physiological Response and Associated Methods filed May 7, 2012, the contents of each of which are incorporated by reference in their entireties except to the extent disclosure therein is inconsistent with disclosure herein.

FIELD OF THE INVENTION

The present invention relates to systems and methods for providing instructions to and operating a lighting device to emit light of varying spectra.

BACKGROUND OF THE INVENTION

Remotely-controllable lighting devices with the capability of emitting light with varied spectral power distribution are increasingly prevalent. Some of these lighting devices are controllable by communicating with the lighting device across a common network, such as a Wi-Fi network, in such networks, and particularly where multiple lighting devices are connected to a single network, a finite bandwidth exists over which to communicate instructions to the lighting devices to change their emission characteristics. Furthermore, that bandwidth may be shared by other devices requiring network capacity for other purposes, such as file transfers within the network, video monitoring, Internet traffic, and the like. Accordingly, there is a need to reduce the amount of bandwidth needed by lighting devices that are controllable across a network so as to minimize usage of network resources.

Other lighting devices communicate using more direct wireless communication standards, such as Bluetooth, Zigbee, and the like. In such lighting devices, particularly in the case of Zigbee, the throughput of the connection between the lighting device and the controlling device may be such that large amounts of data may require significant amounts of time to be transmitted, creating a noticeable delay and potentially resulting in a lack of coordination between lighting devices. Accordingly, there is a need to reduce the amount of data needed to be transmitted to a lighting device so as to avoid such scenarios.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention advantageously enables user control of the spectral power distribution of light emitted by a lighting device while reducing the amount of network traffic required to accomplish such control. Embodiments of the present invention are related to a lighting device comprising a light source including a plurality of light-emitting diodes (LEDs) a control circuit configured to control the operation of the light source and a communication device positioned in communication with the control circuit. The communication device may be configured to receive a transmission from a user device. The transmission may include a data structure. The data structure may comprise a show packet and an event packet. The show packet may comprise an ID string and information regarding a number of event packets associated with the data structure. Additionally, the event packet comprises information regarding a lighting spectrum, a fade type, a fade duration, and a hold duration. Furthermore, the control circuit may be configured to operate the light source to emit light transitioning from a present light emission having a present spectral power distribution to a light emission having spectral power distribution indicated by the lighting spectrum according to the fade type and fade duration, and to operate the light source to emit light having the spectral power distribution indicated by the lighting spectrum for a length of time indicated by the hold duration.

In some embodiments, the control circuit may comprise a plurality of transition points and may be configured to operate the light source so as to transition the spectral power distribution of light emitted by the light source between at least one of the plurality of transition points and the spectral power distribution indicated by the lighting spectrum. Additionally, at least one of the plurality of transition points may correspond to a color of light emitted by a light-emitting diode (LED) of the plurality of LEDs. Furthermore, at least one of the plurality of transition points may correspond to a black body radiation curve color point. The control circuit may be configured to exclude at least one transition point of the plurality of transition points when transitioning from the present spectral power distribution to the spectral power distribution associated with the lighting spectrum.

In some embodiments, the data structure may further comprise a repeat packet. The show packet may further comprise information regarding the number of repeat packets associated with the data structure. Additionally, the event packet may further comprise an indication as to whether the event packet is part of a repeat group. The repeat packet may comprise information regarding repeating one or more event packets associated with the data structure. The show packet may further comprise information regarding the number of repeat packets associated with the data structure.

In other embodiments, the show packet may further comprise information regarding a duration of the data structure. Furthermore, the show packet may further comprise information regarding an ending spectral power distribution to be emitted upon reaching the duration of the data structure. Additionally, the show packet may further comprise information regarding a start time of the data structure. The fade type may be selected from the group consisting of linear fade, exponential fade, logarithmic fade, sinusoidal fade, fade through black, black body fade, and color wheel fade.

Further embodiments of the present invention are related to a method of operating a lighting device comprising a control circuit and a light source, the method comprising the steps of emitting light having an initial spectral power distribution, receiving a data structure comprising a show packet and an event packet, identifying the number of event packets associated with the data structure, identifying a lighting spectrum, a fade type, a fade duration, and a hold duration associated with the data structure, and operating the light source so as to emit light transitioning from the initial spectral power distribution to a light emission having a spectral power distribution indicated by the lighting spectrum, according to the fade type and fade duration, for a length of time indicated by the hold duration. The method may further comprise the step of determining a plurality of transition points responsive to each of the initial spectral power distribution, fade type, and spectral power distribution indicated by the lighting spectrum. In such embodiments, the step of operating the light source may comprise operating the light source so as to transition the spectral power distribution between at least one of the plurality of transition points.

In some embodiments, the light source may comprise a plurality of light-emitting diodes (LEDs). At least one the plurality of transition points may correspond to a color of light emitted by an LED of the plurality of LEDs. Additionally, at least one of the plurality of transition points may correspond to a black body radiation curve color point. Furthermore, at least one transition point of the plurality of transition points may be excluded.

In other embodiments, the data structure further comprises a repeat packet. Furthermore, the method may additionally comprise the steps of identifying the number of repeat packets associated with the data structure, identifying one or more event packets associated with a repeat packet, and operating the light source responsive to the repeat packet.

Additionally, the method may further comprise operating the light source according to a fade type selected from the group consisting of a linear fade, an exponential fade, a logarithmic fade, a sinusoidal fade, a fade through black, a black body fade, and a color wheel fade.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Figure 1:
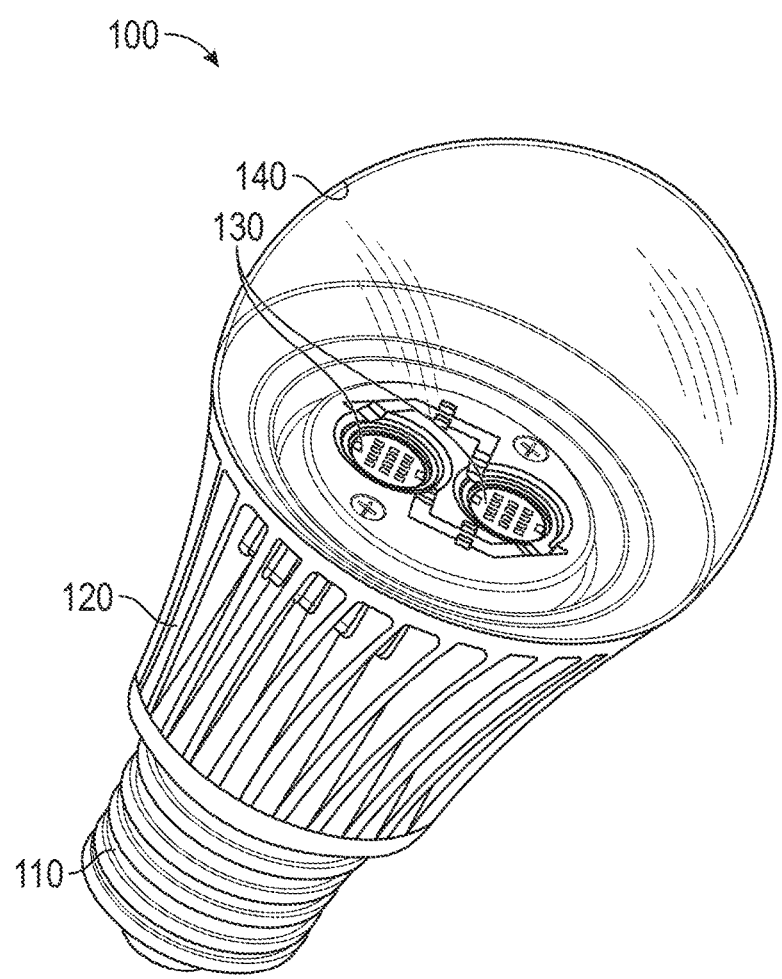
FIG. 1 is a perspective view of a lighting device according to an embodiment of the present invention.
Figure 2:
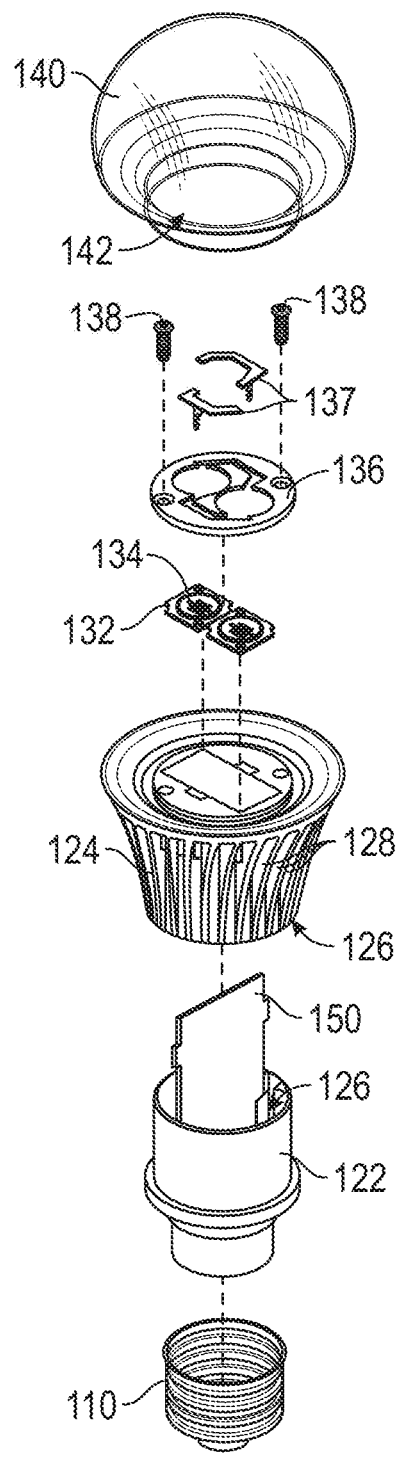
FIG. 2 is an exploded view of the lighting device of FIG. 1.

An embodiment of the invention, as shown and described by the various figures and accompanying text, provides a lighting device configured to emit light having varying spectral power distribution according to differing lighting scenarios, each lighting scenario having a spectral power distribution being configured to have a biological effect in an observer. Referring now to FIGS. 1-2, in the present embodiment, a lighting device 100 is provided. The lighting device 100 may comprise an electrical base 110, a body member 120, a light source 130, an optic 140, and control circuit 150. The electrical base 110 may be configured to engage with and electrically couple to a light socket of a lighting fixture. In the present embodiment, the electrical base 110 is an Edison-type screw base. Any other type base that is known m the art is contemplated to be included within the scope of the invention, including, but not limited to, wedge, bi-pin, and bi-post bases.

The body member 120 may be attached to the electrical base 110. The body member 120 may include a core member 122 and an outer member 124. The core member 122 may be configured to engage with and attach to the electrical base 110. Additionally, the core member 122 may be configured to define a circuit chamber 126. The outer member 124 may be configured to be positioned so as to generally circumscribe or be placed about at least a portion of the core member 122. Additionally, the outer member 124 may be configured to receive and to permit to be attached thereto the light source 130. Additionally, the outer member 124 may be configured to include features adapted to increase the thermal dissipation capacity of the outer member 124, as well as the lighting device 100 generally. For example, the outer member 124 may include a plurality of ribs 128 that serve to increase the surface area of the outer member 124, thereby increasing the thermal dissipation capacity thereof. More information regarding the configuration of the outer member 124 to function in the capacity of a heat sink may be found in U.S. patent application Ser. No. 13/107,782 titled Sound Baffling Cooling System for LED Thermal Management and Associated Methods filed May 13, 2011, the content of which is incorporated in its entirety herein by reference. Additionally, the outer member 124 may cooperate with the core member 122 in defining the circuit chamber 126.

The light source 130 may be configured to be attached to and carried by the body member 120. More specifically, the light source 130 may be configured to be attached to and carried by the outer member 124. The light source 130 may be any type of light-emitting device as is known in the art, including, but not limited to, incandescent light sources, halogen tight sources, fluorescent tight sources and light-emitting semiconductors, more specifically, light-emitting diodes (LEDs). In the present embodiment, the light source 130 may include a light source board 132 comprising a plurality of LEDs 134, the attachment member 136, one or more securing members 137, and one or more fasteners 138, The light source board 132 may be configured to interface with and be carried by the body member 120, or specifically, the outer member 124. Furthermore, the attachment member 136 may be configured to secure the light source board 132 through the use of each of the securing members 137 and the fasteners 138: whereby the fasteners may attach the attachment member 136 two the outer member 124 and whereby the configuration of at least one of the attachment member 136 and the securing members 137 may be configured to prevent the relative motion of the light source board 132 with respect to the attachment member 138, as well as various other elements of the lighting device 100. Additionally, the light source 130 may be positioned in electrical communication with the control circuit 150. More detail regarding the electrical communication therebetween will be provided hereinbelow.

The optic 140 may be configured to be carried by the body member 120 and, more specifically, may be configured to be carried by the outer member 124. The optic 140 may be configured to define an optical chamber 142. The light source 130 may be positioned such that, when operated, light emitted thereby may propagate through the optical chamber 142, out of the optic 140, and into the environment surrounding the lighting device 100. Accordingly, the optic 140 may be formed of any transparent or translucent material. More information regarding the construction and configuration of the optic 140 may be found in U.S. patent application Ser. No. 13/829,832 titled Luminaire with Prismatic Optic filed Mar. 14, 2013, the content of which is incorporated in its entirety herein by reference.

These specific structure of the lighting device 100 as described hereinabove and illustrated in FIGS. 1-2 is exemplary only, and does not limit the scope of the invention described herein below. Any lighting device that is capable of emitting light as described herein below, specifically, having a spectral power distribution as described herein below, is cultivated included within the scope of the invention. The various elements of the lighting device 100, particularly those that are unrelated to the conscience a specific test of emitting light having a spectral power distribution as described hereinbelow, are not essential to the Invention and may be excluded in a given embodiment of the invention.

The control circuit 150 may be configured so as to be positioned within the circuit chamber 126. Additionally, the control circuit 150 may be configured to be positioned in electrical communication with each of the electrical base 110 and the light source 132. The control circuit 150 may be configured to receive electrical power from the electrical base 110. The electrical power may be delivered to the electrical base 110 from an external electricity source. Additionally, the control circuit 150 may include electrical components configured to condition electrical power received from the electrical base 110 for use by the various electrical components of the lighting device 100 including, but not limited to, the light source 130.

The control circuit 150 may be configured to deliver power to and control the operation of the light source 130. More specifically, the control circuit 150 may be configured to operate the plurality of LEDs 134 of the light source 130. In some embodiments, the control circuit 150 may be configured to individually operate each LED of the plurality of LEDs 134.

More details regarding the plurality of LEDs 134 is now provided. The plurality of LEDs 134 may include LEDs configured to emit light having differing peak wavelengths. In some embodiments, the plurality of LEDs 134 may include at least one LED configured to emit light having a peak wavelength at about 420 nm. In some embodiments, the plurality of LEDs 134 may include at least one LED configured to emit light having a peak wavelength at about 450 nm. In some embodiments, the plurality of LEDs 134 may include at least one LED configured to emit light having a peak wavelength at about 540 nm. In some embodiments, the plurality of LEDs 134 may include an LED configured to emit light having a peak wavelength at about 600 nm.

While specific wavelengths of light have been provided hereinabove, it is contemplated and included within the scope of the invention that the plurality of LEDs 134 may include LEDs that are characterized by color as opposed to, or, in addition to, the wavelength of light emitted thereby. Accordingly, the plurality of LEDs 134 may include LEDs configured to emit light that is violet, indigo, blue, cyan, green, yellow, amber, orange, and/or red in color. Moreover, it is contemplated and included within the scope of the invention that the plurality of LEDs 134 may include any combination of LEDs of the colors mentioned hereinabove, as well as any color LED as is known in the art, including white and mint-white LEDs. Additionally, LEDs configured to emit light in the ultraviolet and infrared wavelength ranges may also be included in the plurality of LEDs 134.

Some of the LEDs of the plurality of LEDs 134 may include a color conversion material. The color conversion material may be configured to receive a source light within a first wavelength range and emit a converted light within a second wavelength range that is different from the first wavelength range. In some LEDs, all of the source light emitted by the LED may be converted by the color conversion material, such that no source light is emitted by the LED. Such LEDs may be referred to as fully converted. In some LEDs, a portion of the source light may be converted by the color conversion material, and another portion of the source light may be emitted by the LED, such that light emitted by the LED is a combination of the source light in the converted light. Such LEDs may be referred to as partially converted. LEDs that do not include a color conversion material may be referred to as unconverted. Any type of color conversion material may be used as is known in the art, including, but not limited to, phosphors, quantum dot materials, and dyes, and the like. More information regarding color conversion material may be found in U.S. patent application Ser. No. 13/234,604 titled Remote Light Wavelength Conversion Device and Associated Methods filed Sep. 16, 2011, the content of which is incorporated in its entirety herein by reference.

As recited hereinabove, the control circuit 150 may be configured to control the operation of the plurality of LEDs 134. More specifically, the control circuit 150 may be configured to control the operation of each LED of the plurality of LEDs 134. Accordingly, the control circuit 150 may be configured to control the operation of the LEDs of the plurality of LEDs 134 based upon characteristics of the light emitted thereby. For example, the control circuit 150 may be configured to operate the LEDs of the plurality of LEDs 134 based upon a peak wavelength of light emitted thereby. Accordingly, the control circuit 150 may be configured to control the spectral power distribution of light emitted by the lighting device 100 by controlling the operation of the plurality of LEDs 134 based upon the peak wavelength of light emitted by the operated LEDs.

In addition to being configured to control the operation of each LED of the plurality of LEDs 134, the control circuit 150 may also be configured to control the intensity of light emitted by each LED of the plurality of LEDs 134. The control circuit 150 may control the intensity of light emitted by each LED of the plurality of LEDs 134 by employing any known dimming method as is known in the art, including, but not limited to, pulse-width modulation (PWM) and Sigma-Delta modulation. These methods are exemplary only, and any method known in the art is contemplated to be included within the scope of the invention. Additional information regarding controlling the brightness of light emitted by the LEDs may be found in U.S. Pat. No. 8,492,995 titled Wavelength Sensing Lighting System and Associated Methods filed Oct. 7, 2011 (Ser. No. 13/269,222), the content of which is incorporated in its entirety herein by reference.

By controlling both the spectral power distribution of light emitted by the lighting device 100 by controlling the operation of the LEDs of the plurality of LEDs 134 as well as the level of intensity of the operated LEDs, the control circuit 150 may emit light having selected characteristics. Characteristics include, but are not limited to, brightness, color, color temperature, and color rendering index (CRI). Moreover, the control circuit 150 may be configured to control the spectral power distribution so as to conform to a predetermined spectral power distribution. Some selected spectral power distributions may be configured to affect a biological response in an observer. Some selected spectral power distributions may be configured to avoid affecting a biological response in an observer. More specifically, the selected spectral power distributions may be configured to suppress melatonin secretion in an observer, or to avoid suppressing melatonin secretion in an observer. More information regarding the effect of light on melatonin secretion in an observer of light may be found in U.S. patent application Ser. No. 13/311,300, which is incorporated by reference hereinabove. The control circuit 150 may be configured to operate the plurality of LEDs 134 so as to cause the lighting device 100 to emit light in at least one of a waking-up configuration, a general illumination configuration, a pre-sleep configuration, and a sleep configuration. Moreover, the control circuit 150 may be configured to transition between the various lighting configurations, such that changes to the spectral power distribution of light emitted by the lighting device 100 occur over a period of time so as to be less noticeable to an observer, or with sufficient rapidity that the changes are distinguishable by an observer. More disclosure regarding the various configurations of light is provided hereinbelow.

Figure 3:
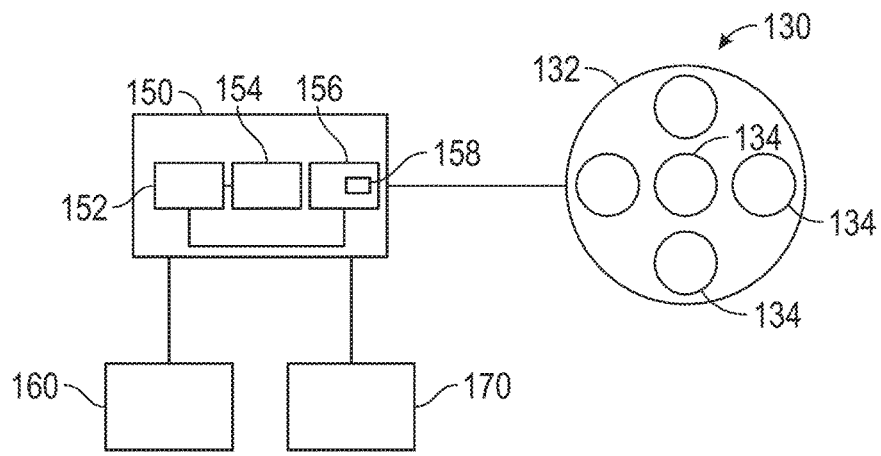
FIG. 3 is a schematic depiction of the lighting device of FIG. 1.

Referring now additionally to FIG. 3, additional elements of the lighting device 100 as depicted in FIGS. 1-2 will now be discussed. The lighting device 100 may include a communication device 160. The communication device 160 may be positioned in electrical communication with the control circuit 150. The communication device 160 may be configured to receive transmissions from a remote computerized device and relay those transmissions to the control circuit 150 in a format that is processable by the control circuit 150.

The communication device 180 may be configured to establish communication across the network. Any type of network that is known in the art is contemplated to be included within the scope of the invention, including, but not limited to personal area networks (PAN), local access networks (LAN), wide area networks (WAN), the Internet, and the like. Additionally, the communication device 160 may be configured to comply with any computerized communication standard as is known in the art, including, but not limited to wired communication, such as Ethernet protocols, universal serial bus (USB) protocols, and the like. With a communication device 160 that is configured to communicate using wired communication, the communication device 160 may include a port configured to receive a communication cable that complies with the wireless communication standard requirements. Additionally, the communication device 160 may be configured to communicate using wifeless communication and may comply with any wireless standard as is known in the art, including, but not limited to, IEEE 802.11 standards, commonly referred to as Wi-Fi, IEEE 802.15 standards including a, b, g, and n standards, Bluetooth, and ZigBee, including the 802.15.4 standard. Additionally, other forms of wireless communication are contemplated and included within the scope of the invention, including, but not limited to, ail other forms of radio communication, infrared communication, visible light communication (VLC), acoustic communication, and the like. More information regarding the communication device 160 may be found in U.S. patent application Ser. No. 13/403,531 titled Configurable Environmental Condition Sensing Luminaire, System and Associated Methods filed Feb. 23,2012, the content of which is incorporated in its entirety herein by reference.

In some embodiments, the control circuit 150 may include a controller 152. The controller 152 may be configured to control the operation of the light source 130 as described hereinabove. More specifically, the controller 152 may include software that enables the controller 152 to operate fie light source 130 as described hereinabove. Accordingly, the controller 152 may be positioned in electrical communication with the light source 130. Furthermore, the controller 152 may be positioned in electrical communication with the plurality of LEDs 134 such that the controller 152 may individually operate each LED of the plurality of LEDs 134. Additionally, the controller 152 may be configured to control the intensity of light emitted by each LED of the plurality of LEDs 152. The controller 152 may be any type of processing device as is known in the art, including, but not limited to, processors, microprocessors, field-programmable gate arrays (FPGA), and the like.

Additionally, the controller 152 may be positioned in electrical communication with the communication device 160. Furthermore, the controller 152 may be configured to receive transmission from the communication device 160 and to operate the light source 130 responsive to transmissions received from the communication device 160. Additional details regarding the operation of the light source 130 responsive to transmissions received from the communication device 160 will be provided hereinbelow.

In some embodiments, the control circuit 150 may include a memory 154. The memory 154 may be positioned in electrical communication with the controller 152. The memory 154 may be configured to be accessible by the controller 152 such that the controller 152 may write data to the memory 154 as well as access and retrieve data stored on the memory 154. The memory 154 may be any volatile or non-volatile memory device as is known in the art including, but not limited to, flash, ROM, PROM, EPROM, EEPROM, RAM, and hard disk drives. In the present embodiment the memory 154 may be a flash memory module or modules, in some embodiments, the controller 152 may be configured to write transmissions received from the communication device 180 onto the memory 154 for subsequent retrieval and execution, as will be discussed in greater detail hereinbelow.

In some embodiments, the control circuit 150 may include a clock 156. The clock 156 may be positioned in electrical communication with the controller 152. The clock 156 may be configured to provide various training information to the controller 152, which the controller 152 may control the operation of the light source 130 responsive to. For example, the clock 156 may provide at least one of a time of day and a measurement of time elapsed between two time points. Additionally, the clock 156 may be configured to be set by the controller 152. Specifically, the clock 156 may be configured to be set by a transmission received by the controller 152, which in turn sets the clock 156 to a time of day.

The clock 156 may have associated therewith a rechargeable power storage device 158. The rechargeable power storage device 158 may be configured to provide power to the clock 158. Moreover, the rechargeable power storage device 158 may be configured to provide power to the clock 156 when electrical power is not presently being provided to the control circuit 150. In this way, when electrical power delivery is restored to the control circuit 150, the clock 156 will have had a continuous power source and may successfully maintain tracking of the time of day. The rechargeable power storage device 158 may be any power storage device as is known in the art, including, but not limited to, capacitors, such as super-capacitors and ultra-capacitors, batteries, and the light. Moreover, the rechargeable powered storage device 158 may be configured to store electrical power when the control circuit 150 is presently being provided with electrical power.

In some embodiments, the lighting device 100 may further include a sensor 170. The sensor 170 may be configured to detect motion and/or occupancy in a field of view of the lighting device. The field of view may be defined as the space in which the sensor 170 is able to detect motion and/or occupancy. The sensor 170 may be positioned in electrical communication with the controller 152. Furthermore, the sensor 170 may be configured to generate and transmit a signal to the controller 152 indicating if motion/occupancy is detected in the field of view of the lighting device 100. Additionally, the controller 152 may be configured to operate responsive to the indication received from the sensor 170. The sensor 170 may be any type of sensing device as is known in the art for detecting motion and/or occupancy. Types of sensors include, but are not limited to, motion detectors, cameras, video capture devices, optical sensors, acoustical sensors, infrared detectors, LEDs, and the like. Additional details regarding the sensor 170 may be found in U.S. patent application Ser. No. 13/464,345 titled Occupancy Sensor and Associated Methods filed May 4, 2012, the content of which is incorporated in its entirety herein by reference, as well as U.S. Pat. No. 8,492,995, which is incorporated by reference hereinabove.

The controller 152 may be configured to operate the light source 130 responsive to an indication received from the sensor 170. More specifically, the controller 152 may be configured to change the spectral power distribution of light emitted by the light source 130 responsive to an indication received from the sensor 170. More specifically, the controller 152 may be configured to infer a level of activity from one or more indications received from the sensor 170. Once a level of activity has been inferred, the controller 152 may determine whether or not to change the illumination configuration of the light source 130. Furthermore, the controller 152 may be configured to associate with each indication received from the sensor 170 a time of day, as indicated by the clock 156. Accordingly, the controller 152 may be configured to alter the illumination of the light source 130 responsive to both an indication received from the sensor 170 as well as the time of day indicated by the clock 156.

Figure 4:
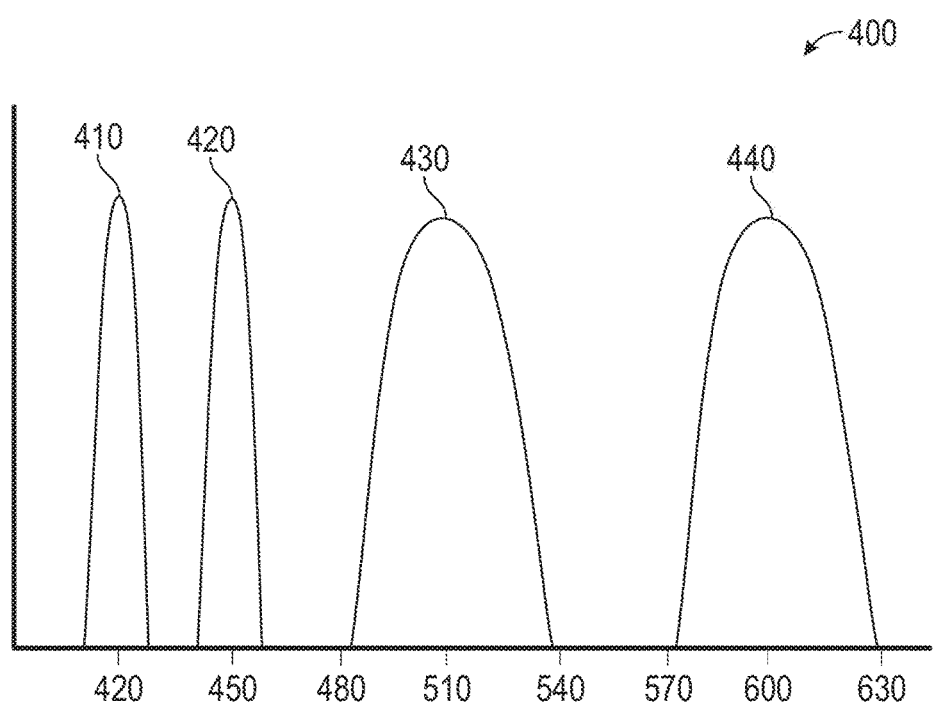
FIG. 4 is a graph of spectral power distributions of light emitted by light-emitting diodes (LEDs) of the lighting device of FIG. 1.

Referring now to FIG. 4, a graph 400 of various spectral power distributions (SPD) of LEDs is presented. As discussed hereinabove, the plurality of LEDs may include LEDs configured to emit light having differing peak wavelengths. The graph 400 depicts the SPD of four types of LEDs that may be included in the plurality of LEDs 134 described hereinabove. Plot 410 illustrates the SPD of a first LED type that is configured to emit light having a peak wavelength at about 420 nm. Plot 420 illustrates the SPD of a second LED type configured to emit light having a peak wavelength at about 450 nm. Plot 430 illustrates the SPD of a third LED type configured to emit light having a peak wavelength at about 510 nm. Plot 440 illustrates the SPD of a fourth LED type configured to emit light having a peak wavelength at about 600 nm, Each of the LEDs illustrated by the Plots 410, 420, 430, 440 may have associated therewith, being violet/indigo, blue, green, and red, respectively. It is contemplated and included within the scope of the invention that the lighting device 100 described hereinabove may include any and all of the LEDs configured to emit light having SPDs represented by the Plots 410, 420, 430, 440, and may include any amount of said LEDs.

Figure 5:
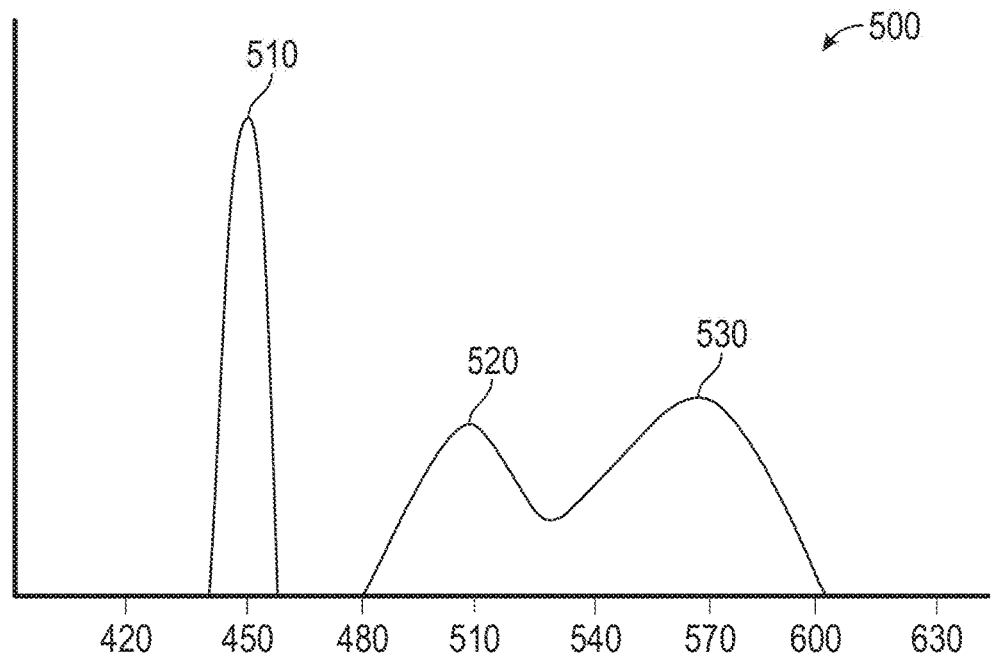
FIG. 5 is a graph of a spectral power distribution of light emitted by the lighting device of FIG. 1 when operated in a phase-shift lighting configuration.

Referring now to FIG. 5, a plot 500 of the spectral power distribution of light emitted by a lighting device is presented. The plot 500 depicts the SPD of light when a lighting device is operated in a wake-up configuration, The wake-up configuration may be configured to affect a biological response in an observer so as to generally increase the real and/or perceived activity level of an observer. Put another way, the wake-up configuration may be configured to increase suppression of melatonin secretion in an observer at a level higher relative to other various illumination configurations. In the wake-up configuration, the plot 500 may include a first peak 510 at about 450 nm, a second peak 520 at about 510 nm, and a third peak 530 at about 580 nm. The first peak 510 may have an intensity that is greater than the intensity either of the second peak 520 or the third peak 530, or both. Moreover, the first peak 510 may have a relative intensity that is within the range from about 125% to about 300% of any other peak intensity of the plot 500.

Figure 6:
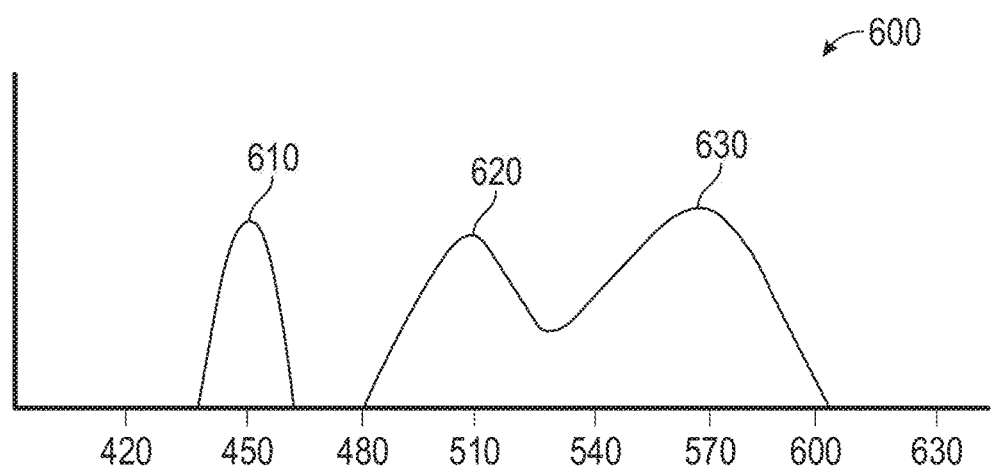
FIG. 6 is a graph of a spectral power distribution of light emitted by the lighting device of FIG. 1 when operated in a general illumination lighting configuration.

Referring now to FIG. 6, a plot 600 of the spectral power distribution of light emitted by a lighting device is presented. The plot 600 depicts the SPD of light when the lighting device is operated in a general illumination configuration. The general illumination configuration may be configured to affect a biological response in an observer so as to maintain a level of suppression of melatonin secretion in an observer. Put another way, the general illumination configuration and be configured to affect suppression of melatonin secretion in an observer at a level that is lower relative to the wake-up configuration, but greater relative to other various illumination configurations, in the general illumination configuration, the plot 800 may include a first peak 610 at about 450 nm, a second peak 820 at about 510 nm, and a third peak 630 at about 580 nm. The first peak 610 may have a relative intensity that is less than or approximately equal to other peak intensities of the plot 600. More specifically, the first peak 610 may have a relative intensity that is within the range from about 50% to about 100% of any other peak intensity of the plot 600.

Figure 7:
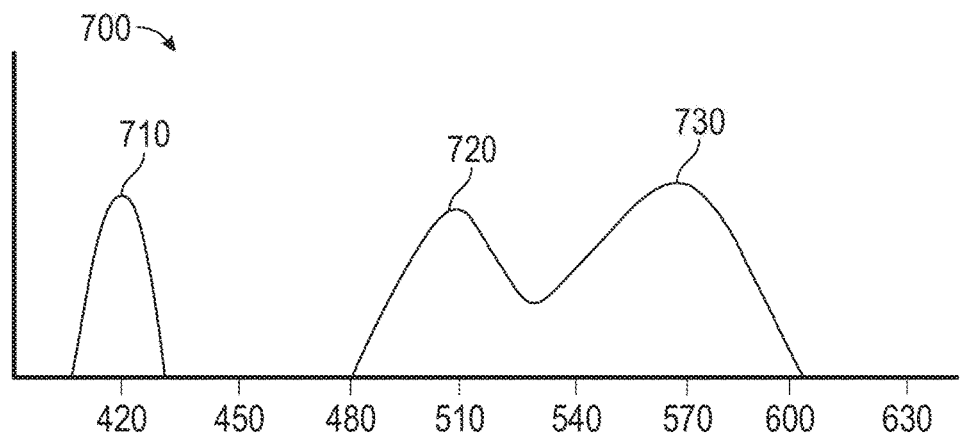
FIG. 7 is a graph of the spectral power distribution of light emitted by the lighting device of FIG. 1 when operated in a pre-sleep lighting configuration.

Referring now to FIG. 7, a plot 700 of the spectral power distribution of light emitted by a lighting device is presented. The plot 700 depicts the SPD of light when a lighting device is operated in a pre-sleep configuration. The pre-sleep configuration may be configured to affect biological response in an observer so as to promote the onset of sleepiness in an observer. More specifically, the pre-sleep configuration may be configured to affect a decrease in the suppression of melatonin secretion in an observer. In the pre-sleep configuration, the plot 700 may include a first peak 710 at about 420 nm, a second peak 720 at about 540 nm, and a third peak 730 at about 580 nm. A peak intensity that about 420 nm will a fact a lower level of melatonin secretion suppression in an observer relative to a peak at about 450 nm while still enabling the lighting device that is emitted in light having an SPD corresponding to the plot 700 to emit light having certain characteristics. For example, the light having an SPD corresponding to the plot 700 may be a generally white light and may have a higher CRI than light that does not include a peak within the range from about 420 nm to about 490 nm. In this way, a lighting device that is emitting light having an SPD corresponding to the plot 700 may emit light that has desirable lighting characteristics while also avoiding suppressing the secretion of melatonin to a significant extent. The first peak 710 may have a relative intensity that is less than or approximately equal to other peak intensity of the plot 700. More specifically, the first peak 710 may have a relative intensity that Is within the range from about 50% to about 100% of any other peak intensity of the plot 700.

Figure 8:
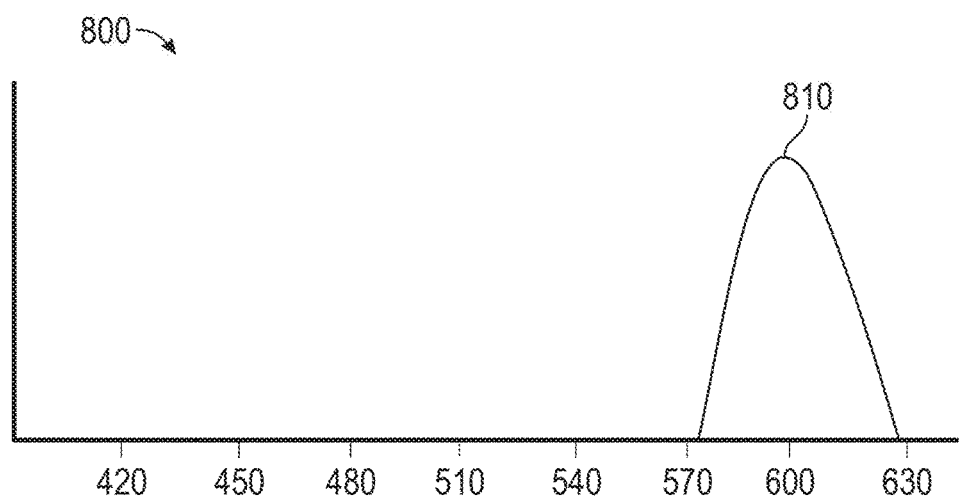
FIG. 8 is a first graph of the spectral power distribution of light emitted by the lighting device of FIG. 1 when operated in a sleep lighting configuration.

Referring now to FIG. 8, a plot 600 of the spectral power distribution of light emitted by a lighting device is presented. The plot 800 depicts the SPD of light when a lighting device is operated in a sleep configuration. The steep configuration may be configured to affect a biological response in an observer so as to promote the onset of sleepiness in an observer. More specifically, the sleep configuration may be configured to affect a decrease in the suppression of melatonin secretion in an observer relative to each of the wake-up, general illumination, and pre-sleep configurations. In the sleep configuration, the plot 800 may include a peak 810 at about 600 nm. It is recognized that light having an SPD corresponding to the plot 800 may have characteristics significantly different from the other illumination configurations, including reduced brightness, reduced CRI, and being a generally "colored" light and, more specifically, a red light. The sleep configuration is contemplated for use during sleeping hours, when increased brightness and high CRI are less important than in time periods associated with the use of the various other illumination configurations. Furthermore, in some embodiments, the sleep configuration may be configured such that light within the wavelength range from about 430 nm to about 490 nm has an intensity that is less than 10% of the intensity of peak 610 in FIG. 6. Furthermore, in some embodiments, the sleep configuration may be configured such that light within the wavelength range from about 430 nm to about 490 nm has an intensity that is less than or approximately equal to about 5% of the intensity of peak 810 in FIG. 6.

Figure 9:
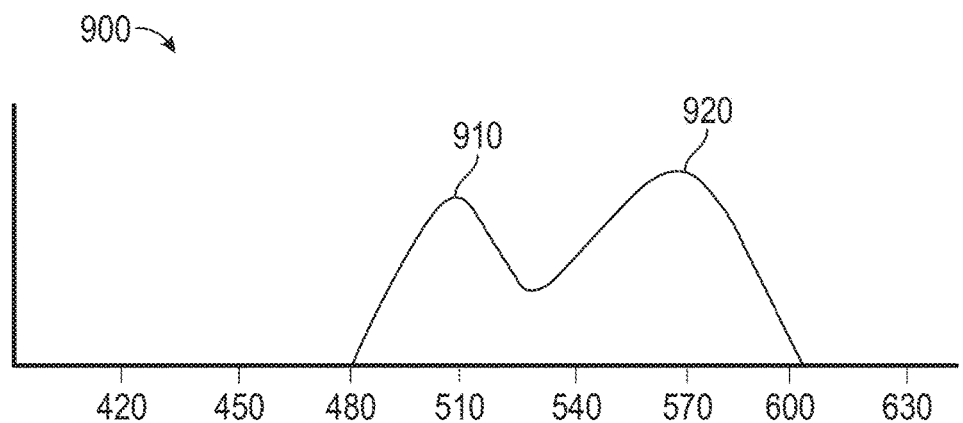
FIG. 9 is a second graph of the spectral power distribution of light emitted by the lighting device of FIG. 1 when operated in a sleep lighting configuration.

Referring now to FIG. 9, a plot 900 of the spectral power distribution of light emitted by a lighting device is presented. The plots 900 depicts the SPD of light with a lighting device is operated in a sleep configuration, the present sleep configuration being an alternative embodiment to the sleep configuration depicted in FIG. 8. The present sleep configuration that is illustrated in FIG. 9 may be configured to have a similar biological response in an observer to that of the light whose SPD is represented in FIG. 8, namely, promoting the onset of sleepiness in an observer, and more specifically, affecting a decrease in the suppression of melatonin secretion in an observer relative to each of the wake-up, and general illumination, and pre-fleet configurations. In the present embodiment of the sleep configuration, the plots 900 may include a first peak 910 at about 540 nm and a second peak 920 at about 600 nm. It is recognized that light having an SPD corresponding to the plot 900 may have characteristics significantly different from the wake-up, the general illumination, and pre-fleet configurations, including reduced brightness, reduced CRI, and being a generally "colored" light, more specifically, a yellow light, resulting from the combination of a generally green light, as represented by the first peak 910, with a generally red light, as represented by the second peak 920. It is appreciated that, while the present embodiment of the sleep configuration may result in greater suppression of melatonin secretion in an observer, the configuration also emit light having increased CRS relative to the embodiment of the sleep configuration represented in FIG. 8, and thus may be desirable.

Referring now to FIGS. 1-9, a mode of operation of the lighting device 100 will now be discussed. The lighting device 100 may be configured to emit light in the various illumination configurations described hereinabove responsive to transmissions received by the medication device 160. Additionally, the lighting device 100 may have an initial configuration to emit light in the various illumination configurations described hereinabove in a particular pattern. More specifically, the controller 152 may have an initial configuration to emit light in the various illumination configurations described hereinabove in a particular pattern dependent upon the time of day indicated by the clock 156. For example, the memory 154 may have stored thereon a sequence of instructions 158 that are accessible by the controller 152 that may cause the controller 152 to operate the plurality of LEDs 134 emit light according to the various illumination configurations at different times of the day. Also for example, a first step in the sequence of instructions 158 may cause the controller 152 to operate the plurality of LEDs 134 so as to cause the lighting device 100 to emit light having a spectral power distribution approximately conforming to the plot 500, conforming to the wake-up configuration during a time period associated with the morning, such as, for example, 6 AM to 8 AM. Furthermore, a second step in the sequence of instructions 158 may cause the controller 152 to operate the plurality of LEDs 134 so as to cause the lighting device 100 to emit light having a spectral power distribution approximately conforming to the plot 600, conforming to the general illumination configuration during a time period associated with the daytime, such as, for example, 9 AM to 3 PM. Furthermore, a third step in the sequence of instructions 158 may cause the controller 152 to operate the plurality of LEDs 134 so as to cause the lighting device 100 to emit light having a spectral power distribution approximately conforming to the plot 500, conforming to the wake-up configuration during a time period associated with the afternoon, such as, for example, 3 PM to 5 PM, Furthermore, a fourth step in the sequence of instructions 158 may cause the controller 152 to operate the plurality of LEDs 134 so as to cause the lighting device 100 to emit light having a spectral power distribution approximately conforming to the plot 700, conforming to the pre-sleep configuration during a time period associated with the evening, such as, for example, 5 PM to 10 PM. Furthermore, a fifth step in the sequence of instructions 158 may cause the controller 152 to operate the plurality of LEDs 134 so as to cause the lighting device 100 to emit light having a spectral power distribution approximately conforming to the plot 800, conforming to the sleep configuration during a time period associated with sleeping, such as, for example, 10 PM to 6 AM. Moreover, the final step in the sequence of instructions 158 may cause the controller 152 to return to the first step described hereinabove. The hours provided hereinabove for each of the steps in the sequence of instructions 158 are exemplary only, and deviations therefrom are contemplated to be included within the scope of the invention.

As described hereinabove, the controller 152 may receive from the clock 156 indications of the time of day. Accordingly, the transitions between the steps described herein may initiate upon the controller 152 receiving an indication of the time of day from the clock 156 that corresponds to a change in the illumination configuration.

Furthermore, the controller 152 may be configured to alter the times of the transmissions between the various illumination configurations responsive to one or more indications from the sensor 170. For example, the controller 152 may be configured to identify patterns of activity based upon a plurality of indications received from the sensor 170. Methods of pattern recognition are detailed in U.S. Provisional Patent Application Serial No. 81/336,654 titled System for Detecting and Analyzing Motion for Pattern Predication and Associated Methods filed Feb. 6, 2014, which is incorporated by reference herein in its entirety.

The controller 152 may alter the times of day that the transitions between illumination configurations occur based on identified patterns, More specifically, the controller 152 may be configured to identify a periods of levels of activity that may correspond to various predicted activities during the day, which may in tern be associated with one of the illumination configurations. For example, the controller 152 may be configured to determine an approximate time of waking based upon an increase of the frequency of indications received from the controller 152 within a time range associated with waking, such as, for example, between 5 AM and 8 AM, If the controller 152 received indications indicating a pattern of increased level of activity within the range from 7 to 7:30 AM, the controller 152 may be configured to operate the light source 130 to emit light corresponding to the wake-up configuration beginning at about 7 AM. Similarly, if the controller 152 received indications indicating a pattern of increased level of activity within the range from about 5 to about 5:30 AM, the controller 152 may operate the light source 130 to emit light corresponding to the wake-up configuration beginning at about 5 AM, Moreover, the controller 152 may be configured to continuously adjust the time at which to emit light corresponding to the wake-up configuration responsive to the indications received from the sensor 170.

Additional scenarios are similarly contemplated for the other various illumination configurations. In some embodiments, the controller 152 may be configured to interpret indications indicating a pattern of a consistent level of activity within the range from about 9 AM to about 12 PM. For example, the controller 152 may receive such an indication at about 10 AM. In such embodiments, the controller 152 may be configured to operate the light source 130 to emit light corresponding to the general illumination configuration beginning at about 10 AM. In some embodiments, the controller 152 may be configured to interpret indications indicating a pattern of a slightly reduced activity level within the range from about 12 PM to about 5 PM. For example, the controller 152 may receive such an indication at about 2 PM. In such embodiments, the controller 152 may be configured to operate the light source 130 to emit light corresponding to the wake-up configuration beginning at about 2 PM. In some embodiments, the controller 152 may be configured to interpret indications indicating a pattern of a decreased level of activity within the range from about 5 PM to about 9 PM. For example, the controller 152 may receive such an indication at about 8 PM. In such embodiments, the controller 152 may be configured to operate the light source 130 to emit light corresponding to the pre-sleep configuration beginning at about 8 PM. Additionally, in some embodiments, the controller 152 may receive an indication indicating a pattern of activity level consistent with sleeping within the range from about 8 PM to about 6 AM. For example, the controller 152 may receive such an indication at about 10 PM. The controller 152 may be configured to operate the light source 130 to emit light corresponding to the sleep configuration at about 10 PM. Additionally, the controller 152 may be configured to operate the light source 130 to emit light corresponding to the pre-fleet configuration approximately one hour before the sleep-like pattern of activity is indicated, at about 9 PM.

Additionally, the controller 152 may be configured to keep track of the day of the week and alter the operation of the light source 130 responsive thereto. More specifically, the controller 152 may be configured to receive an indication as to the present day of the week from an external source, such as a user device as described hereinbelow. The controller 152 may subsequently track the day of the week by monitoring the indicated time of day from the clock 156 and calculating when the day of the week changes. Furthermore, the controller 152 may identify patterns of behavior based on the day of the week, similar to how the controller 152 may identify patterns based on the time of day. For example, the controller 152 may identify a first set of patterns based on the time of day for weekdays, and a second set of patterns based on the time of day for weekends, to reflect differences in patterns of behavior associated with the traditional work week. The weekday/weekend dichotomy is exemplary only, and it is contemplated and included within the scope of the invention that patterns for any day or subset of days of the week may be identified and responded to.

Additionally, in some embodiments, the controller 152 may be configured to operate the light source 130 to emit light so as to affect a shift in the circadian rhythm of an observer. More specifically, the controller 152 may be configured to operate the light source 130 either to affect or avoid a biological response in an observer, such as the suppression of secretion of melatonin, as discussed hereinabove. More information regarding affecting a circadian shift may be found in U.S. Provisional Patent Application Ser. No. 61/785,209 titled Method for Controlling Blood Glucose Production which is incorporated by reference hereinabove.

The present circadian rhythm of an observer may be determined by any means or method known in the art. In some embodiments, a circadian rhythm may be provided to the controller 152 by a user, who may be the observer, by entry into a computerized device, such as a user device as described in greater detail hereinbelow. Additionally, in some embodiments, the controller 152 may be configured to determine a circadian rhythm of an observer by interpreting information received from a sensor or device positioned in communication with the controller and configured to provide information related to the determination of a circadian rhythm. Such devices may be configured to indicate whether an observer is awake or asleep. Such devices may include, but are not limited to, wearable devices configured to indicate motion by the wearer. Extended periods without motion may be interpreted by the controller 152 to indicate sleep. Accordingly, a circadian rhythm may be determined by the controller 152 to correspond to the period of time during which sleep is indicated by the device.

Figure 10:
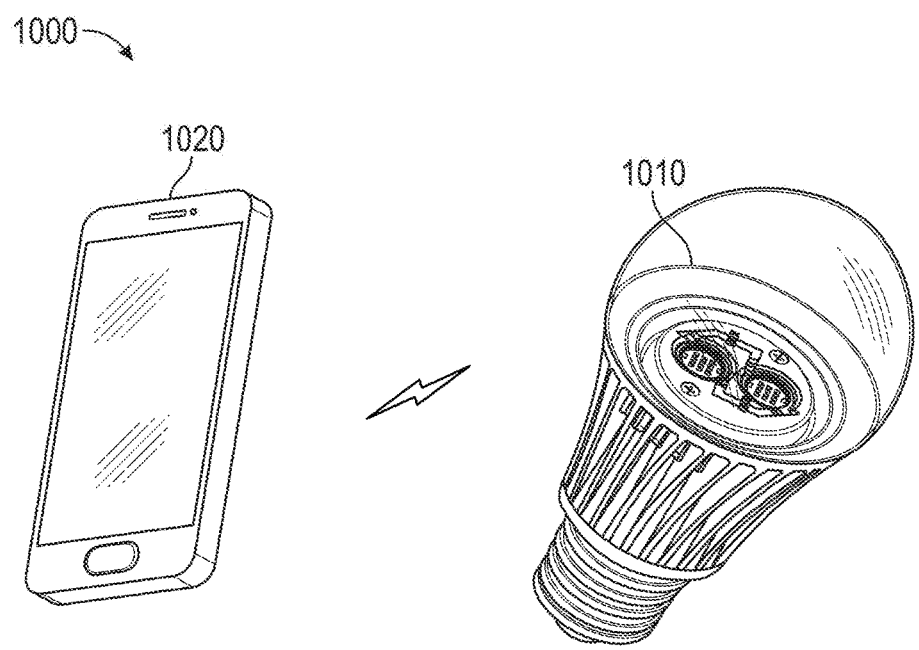
FIG. 10 is an environmental view of a system for controlling the operation of the lighting device of FIG. 1 according to an embodiment of the present invention.

Referring now to FIG. 10, an environmental view of a system 1000 for controlling the lighting device described above and depicted in FIGS. 1-9 is presented. As may be seen in FIG. 10, a lighting device 1010 is presented. The lighting device 1010 may be a lighting device substantially as described hereinabove. The system 1000 further includes a user device 1020. The user device 1020 may be any device capable of being positioned in communication with the communication device 160 as described hereinabove. In some embodiments, the user device 1020 may be a computerized device, including a smart phone, a tablet computer, or a personal computer, such as a desktop computer or a notebook computer. The devices listed are exemplary only, and any device capable of communicating with the communication device 160 is contemplated and included within the scope of the invention.

As described hereinabove, the lighting device 1010 may be configured to receive transmissions from the user device 1020 and operate responsive to the transmissions. More specifically, in some embodiments, the lighting device 1010 may be configured to receive a transmission from the user device 1020 including an instruction for the lighting device 1010 to transition from one illumination configuration to another. Additionally, in some embodiments, the lighting device 1010 may be configured to receive a transmission from the user device 1020 that includes a sequence of instructions, similar to those described hereinabove, for the lighting device 1010 to transition between the various illumination configurations. Furthermore, the user device 1020 may be configured to transmit said instructions along with timing instructions as described hereinabove. Additionally, the user device 1020 may include a user input device capable of receiving inputs from a user. Any type of user input device as is known in the art may be used, including, but not limited to a keyboard, a mouse, a touchscreen, and the like. Moreover, the user device 1020 may include software configured to enable the user to select the desired illumination configurations recited hereinabove, as well as the times of day during which the configurations are to be emitted by the lighting device 1010. Additionally, the user device 1020 may include software that enables the user to define a new lighting configuration by permitting the user to define relative intensities of each of the LEDs of the plurality of LEDs 134.

Figure 11:
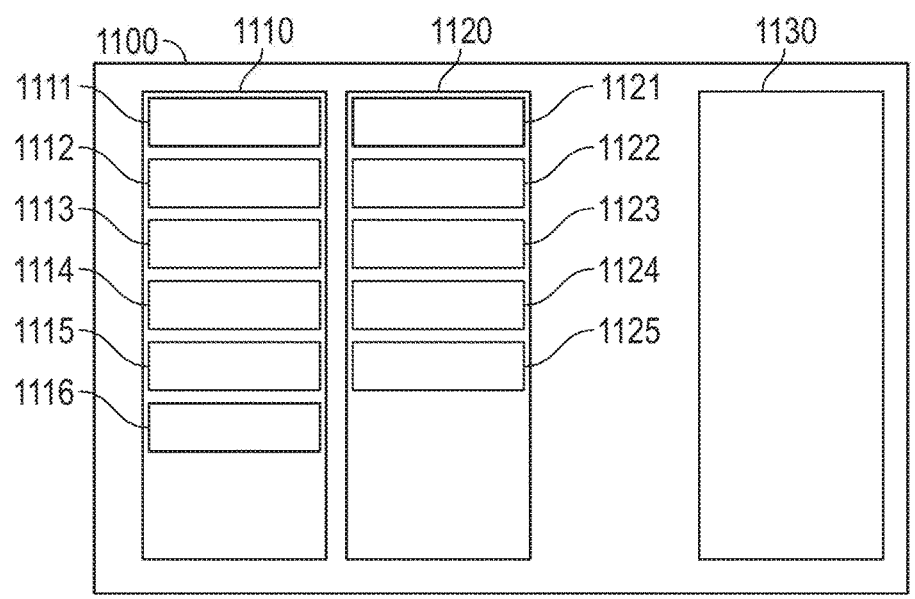
FIG. 11 is a schematic view of a data structure of a program for controlling the operation of the lighting device of FIG. 1 using the system illustrated in FIG. 10.

Referring now to FIG. 11, a data structure 1100 of the transmission by the user device 1020 of FIG. 10 is depicted. The data structure 1100 may be configured to include instructions that the lighting device 1010 of FIG. 10 may operate responsive to, altering the SPD of light emitted thereby. The data structure 1100 may include a show packet 1110, one or more event packets 1120, and, optionally, one or more repeat packets 1130.

The data structure 1100 may be configured such that each constituent element of the data structure 1100 is transmittable by a user device 1020 as depicted in FIG. 11 above, and receivable by a lighting device 1010. More specifically, each of the show packet 1110. event packet 1120, and repeat packet 1130 may be transmittable individually of each other Moreover, the constituent elements of the data structure 1100 may be writable to a memory and retrievable therefrom, such that a given data structure 1100 may be retained by a lighting device and recalled and executed upon receiving such an instruction.

The show packet 1110 may be configured so as to provide information regarding overarching information about the sequence of events to follow. The show packet 1110 may include an ID string 1111, an optional start time 1112, an optional show duration, an optional ending SPD 1114, the number of event packets in the show 1115, and the number of repeat packets in the show 1116. The ID string 1111 may identify the show packet 1110 so as to be differentiate by the lighting device 1010 from any other show received thereby. The start time 1112 may indicate a time of day for which the event is to take place. The show duration 1113 may indicate the length of time for which a show is to take place, in the absence of a show duration 1113, the lighting device 1010 will continue to perform the show until an instruction is received instructing otherwise. The ending SPD 1114 may be a spectral power distribution that is emitted by the lighting device 1010 upon reaching the show duration 1113. The number of event packets in the show 1115 may indicate to the lighting device 1010 the number of event packets 1120, such that an independent determination is not required to be performed by the lighting device 1010. Similarly, the number of repeat packets in the show 1116 may indicate to the lighting device 1010 the number of repeat packets 1130, such that an independent determination is not required to be performed by the lighting device 1010.

The event packets 1120 may provide details regarding transitions between illumination configurations. More specifically, the event packets 1120 may include a lighting spectrum 1121, a fade type 1122, a fade duration 1123, a hold duration 1124, and an indication as to whether or not the event packet is part of a repeat group 1125. The lighting spectrum 1121 may be any type of indication that the lighting device 1010 may interpret and emit light having a particular SPD responsive thereto. Accordingly, the lighting spectrum may be any of an SPD, a color point on a color chart, and instructions for whether or not to operate particular LEDs of the plurality of LEDs 134 as described hereinabove and depicted in FIGS. 1-2, as well as the intensity at which to operate the LEDs, as well as any other method of conveying color information as is known in the art. More information regarding the conveyance of color information and interpretation thereof may be found in U.S. patent application Ser. No. 13/737,606 titled Tunable Light System and Associated Methods filed Jan. 9, 2013, the content of which is incorporated in its entirety herein by reference.

The fade type 1122 may indicate to the lighting device 1010 how to transition from one illumination configuration to another. More specifically, the fade type may indicate to the lighting device what the SPD of the lighting device 1010 should be when transitioning between illumination configurations. It may be understood and appreciated that for each illumination configuration, each LED of the plurality of LEDs may have an associated intensity. That intensity may be zero or non-zero. Moreover, it is appreciated that the intensity of each LED may be controlled by any of the dimming methods disclosed hereinabove. Accordingly, each fade type may be a description of how the lighting device 1010 controls the intensity of each LED of the plurality of LEDs when transitioning between a first intensity associated with a first illumination configuration to a second intensity associated with a second illumination configuration.

One fade type is a linear fade, whereby each LED of the plurality of LEDs is operated so as to transition from a first intensity from a second intensity linearly, meaning the rate of change of the intensity remains constant throughout the duration of the fade. Another fade type is an exponential fade, whereby the rate of change of the intensity increases exponentially throughout the duration of the fade. Yet another fade type is a logarithmic fade, whereby the rate of change of the intensity decreases logarithmically throughout the duration of the fade. Still another fade type is a sinusoidal fade, whereby the rate of change of the intensity varies sinusoidally about a linear rate of change, such that the average rate of change across the duration approximately equals the linear rate of change, but the instantaneous rate of change may be greater or less than the linear rate of change. Another fade type is a fade through black, whereby the intensity of each LED is reduced from its intensity in the first illumination configuration to zero, then each LED having a non-zero intensity in the second illumination configuration is increased to its intensity for the second illumination configuration. The fade through black fade may employ any of the linear, exponential, logarithmic, and sinusoidal fades in transitioning to and from the zero intensity.

Figure 12:
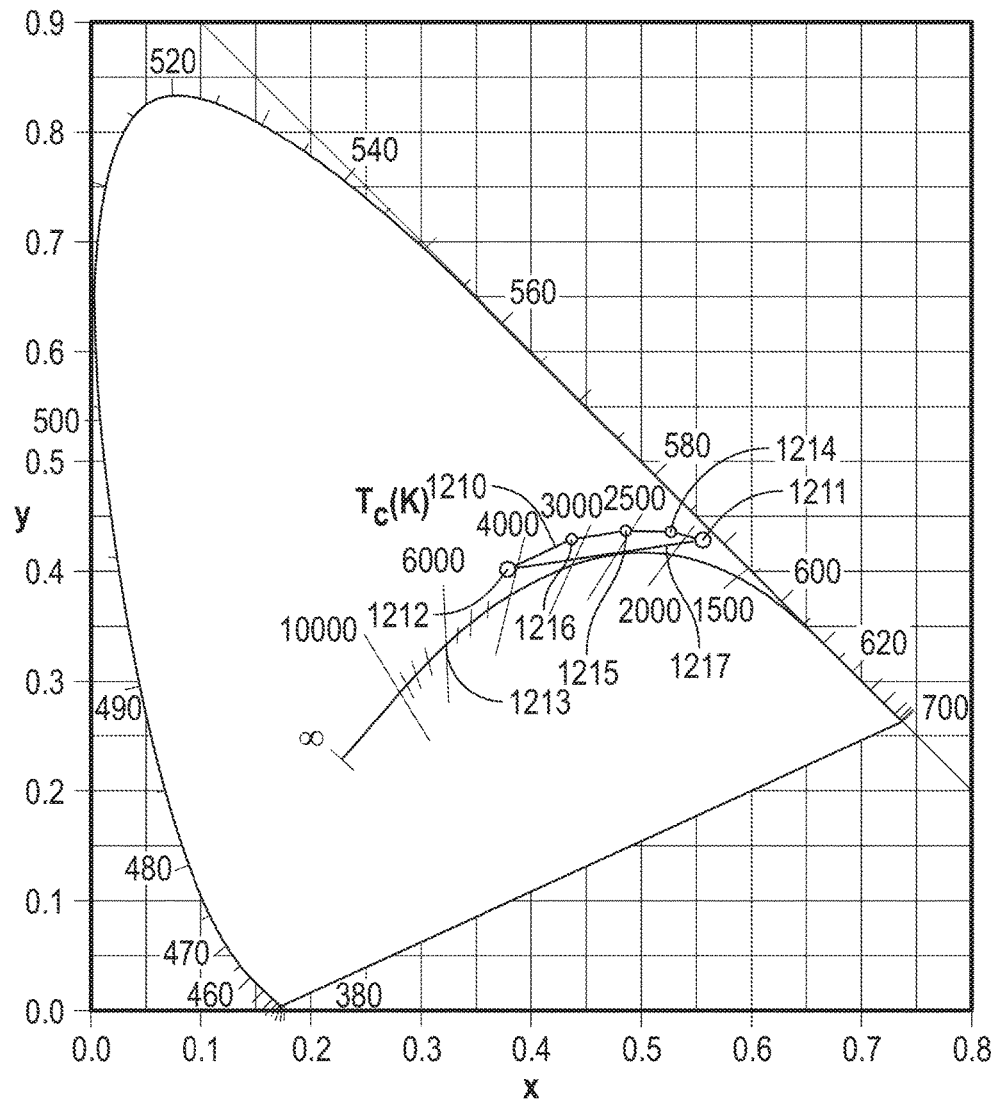
FIGS. 12 and 13 are graphical illustrations of a plot of a mode of transitioning between color points in a color space.

Another fade type is a black body fade, whereby the SPD of light emitted by the lighting device 1010 is configured to follow the black body radiation curve as is known in the art. Referring now to FIG. 12, a plot 1210 may illustrate a transition as described. The plot 1210 may depict a first color temperature 1211 representing the first illumination configuration, as well as a second color temperature 1212 representing the second illumination configuration. The lighting device 1010, more specifically the controller 152 as described hereinabove, may be configured to interpolate one or more transition points. In the present embodiment, the lighting device 1010 creates three transition points 1214, 1215, 1216. It is contemplated and included within the scope of the invention that any number of transition points may be created. Moreover, in some embodiments, no transition points may be created. Each transition point may be a point along the black body radiation curve 1213, such that each transition between the transition points has a reduced deviation from the black body radiation curve 1213 relative to a transition 1217 between the first and second color temperatures 1211, 1212. Similar to the fade through black, the black body fade may employ any of the linear, exponential, logarithmic, and sinusoidal fades in transitioning between the first and second color temperatures 1211, 1212 and, if present, the transition points 1214, 1215, 1216.

Figure 13:
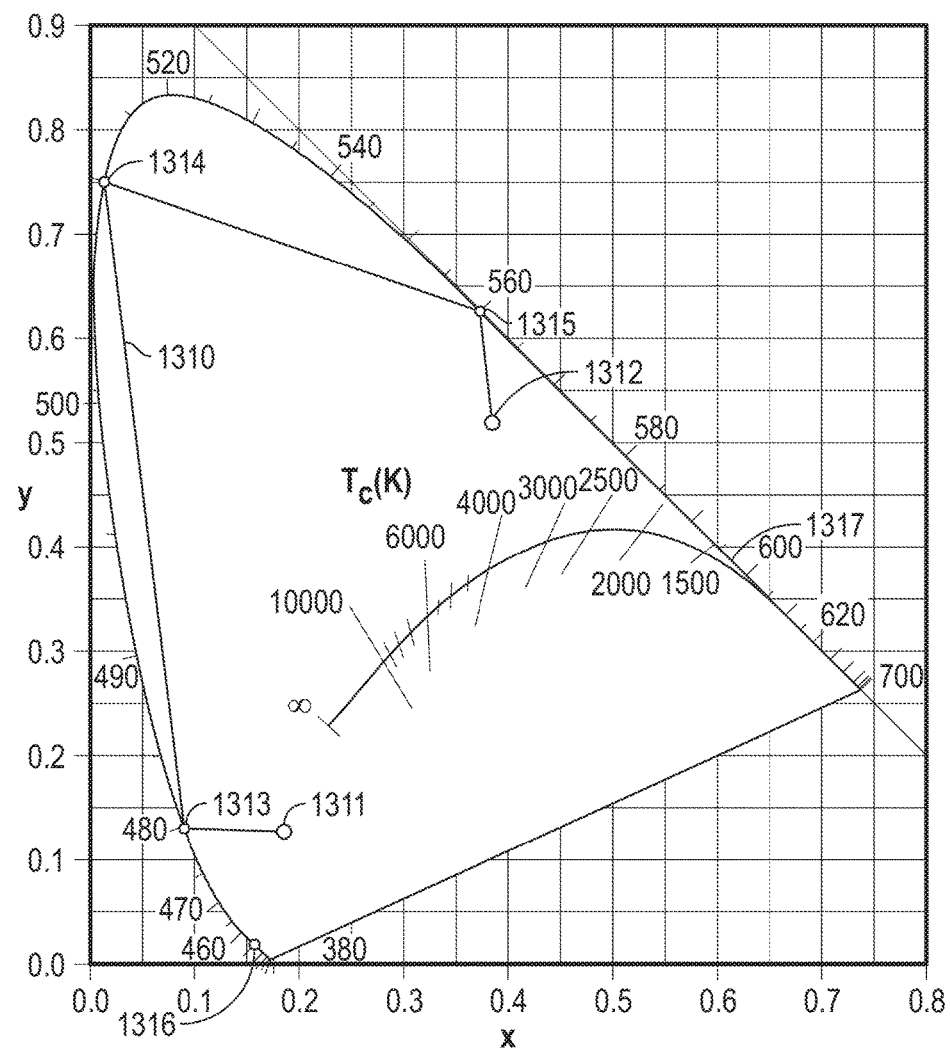

Another fade type is a color wheel fade, whereby the SPD of light emitted by the lighting device 1010 may follow a predetermined transition between colors. For example, as depicted in FIG. 13, a standard color space may have a predetermined color transition as follows: violet:indigo:blue:cyan:green:yellow:amber:orange:red. Moreover, the recited color transition may be generally regarded as a clockwise transition. Accordingly, the reverse may be considered a counterclockwise transition. Accordingly, the color wheel fade may be either clockwise or counterclockwise.

A sample color wheel fade is illustrated by the plot 1310 in FIG. 13. In the present embodiment, the plot 1310 may depict a transition between a first illumination configuration point 1311 and a second illumination configuration point 1312. Each of the first and second illumination configuration points 1311, 1312 may represent the light emitted by the lighting device 1010 when in an illumination configuration, either as defined hereinabove or in a user-defined illumination configuration. While the first and second illumination configuration points 1311, 1312 are represented at certain positions in the color space, it is contemplated and included within the scope of the invention that they may be positioned at any position within the color space that is capable of being emitted by the lighting device. More details regarding the ability of the lighting device 1010 to emit color within the color space may be found in U.S. patent application Ser. Nos. 13/775,936 and 13/737,606, each of which are incorporated by reference hereinabove.

Similar to the plot 1210 of FIG. 12, the plot 1310 may define one or more transition points 1313, 1314, 1315. In some embodiments, each transition point may represent the color of light emitted by an LED of the plurality of LEDs, whereby the color corresponds to the peak wavelength of the LED. The lighting device may be configured to transition from the first illumination configuration point 1311 to the first transition point 1313, then to the second transition point 1314, and then to the third transition point 1315, then transitioning to the second illumination configuration point 1312. It is contemplated and included within the scope of the invention that any number of transition points may be included, including none. Furthermore, in some circumstances, the lighting device 1010 may determine that one or more transition points 1316, 1317 may be excluded from the fade, as illustrated by plot 1310. This may be due to one or both of the first and second illumination configuration points 1311, 1312 having a primary peak wavelength that is either greater or less than a transition point relative to the other of the first and second illumination configuration points 1311 1312.

Referring now back to FIG. 11, the repeat packets 1130 will now be discussed. The repeat packets 1130 may be configured to repeat a subset of the event packets 1120 of the data structure 1100. For example, where data structure includes event packets numbered 1 through 10, a repeat packet 1130 may identify a subset, such as events 2-4, of the event packets to repeat.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A lighting device comprising:
    a light source comprising a plurality of light-emitting diodes (LEDs);
    a control circuit configured to control the operation of the light source; and
    a communication device positioned in communication with the control circuit;
    wherein the communication device is configured to receive a transmission;
    wherein the transmission comprises a data structure;
    wherein the data structure comprises an event packet;
    wherein the event packet comprises information regarding a lighting spectrum, a fade type, and a fade duration; and
    wherein the control circuit is configured to operate the light source to emit light transitioning from a present light emission having a present spectral power distribution to a light emission having spectral power distribution indicated by the lighting spectrum according to the fade type and fade duration, and to operate the light source to emit light having the spectral power distribution indicated by the lighting spectrum.

2. The lighting device of claim 1 wherein the control circuit is configured to operate the light source so as to transition the spectral power distribution of light emitted by the light source between at least one of a plurality of transition points and the spectral power distribution indicated by the lighting spectrum.

3. The lighting device of claim 2 wherein at least one of the plurality of transition points corresponds to a color of light emitted by an LED of the plurality of LEDs.

4. The lighting device of claim 2 wherein at least one of the plurality of transition points corresponds to a black body radiation curve color point.

5. The lighting device of claim 2 wherein the control circuit is configured to exclude at least one transition point of the plurality of transition points when transitioning from the present spectral power distribution to the spectral power distribution associated with the lighting spectrum.

6. The lighting device of claim 1 wherein the data structure further comprises a show packet.

7. The lighting device of claim 6 wherein the show packet further comprises an ID string and information regarding a duration of the data structure.

8. The lighting device of claim 7 wherein the show packet further comprises information regarding an ending spectral power distribution to be emitted upon reaching the duration of the data structure.

9. The lighting device of claim 6 wherein the show packet further comprises information regarding a start time of the data structure.

10. The lighting device of claim 6 wherein the data structure further comprises a repeat packet; wherein the event packet further comprises an indication as to whether the event packet is part of a repeat group; and wherein the repeat packet comprises information regarding repeating one or more event packets associated with the data structure.

11. The lighting device of claim 10 wherein the show packet further comprises information regarding a number of repeat packets associated with the data structure.

12. The lighting device of claim 1 wherein the fade type is selected from the group consisting of linear fade, exponential fade, logarithmic fade, sinusoidal fade, fade through black, black body fade, and color wheel fade.

13. The lighting device of claim 1 wherein the communication device is configured to receive a transmission from a user device.

14. The lighting device of claim 1 wherein the event packet further comprises information regarding a hold duration; and wherein the control circuit is configured to operate the light source to emit light having the spectral power distribution indicated by the lighting spectrum for a length of time indicated by the hold duration.

15. A lighting device comprising:
a light source comprising a plurality of light-emitting diodes (LEDs);
a control circuit configured to control the operation of the light source; and
a communication device positioned in communication with the control circuit;
wherein the communication device is configured to receive a transmission;
wherein the transmission comprises a data structure;
wherein the data structure comprises an event packet;
wherein the event packet comprises information regarding a lighting spectrum, a fade type, and a fade duration; and
wherein the control circuit is configured to operate the light source to emit light transitioning from a present light emission having a present spectral power distribution to a light emission having spectral power distribution indicated by the lighting spectrum according to the fade type and fade duration, and to operate the light source to emit light having the spectral power distribution indicated by the lighting spectrum;
wherein the control circuit is configured to operate the light source so as to transition the spectral power distribution of light emitted by the light source between at least one of a plurality of transition points and the spectral power distribution indicated by the lighting spectrum; and
wherein the fade type is selected from the group consisting of linear fade, exponential fade, logarithmic fade, sinusoidal fade, fade through black, black body fade, and color wheel fade.

16. The lighting device of claim 15 wherein the event packet further comprises information regarding a hold duration; and wherein the control circuit is configured to operate the light source to emit light having the spectral power distribution indicated by the lighting spectrum for a length of time indicated by the hold duration.

17. The lighting device of claim 15 wherein the data structure further comprises a show packet; and wherein the show packet comprises an ID string and information regarding a number of event packets associated with the data structure.

18. The lighting device of claim 17 wherein the show packet further comprises information regarding an ending spectral power distribution to be emitted upon reaching the duration of the data structure.

19. The lighting device of claim 17 wherein the data structure further comprises a repeat packet; wherein the event packet further comprises an indication as to whether the event packet is part of a repeat group; and wherein the repeat packet comprises information regarding repeating one or more event packets associated with the data structure.

20. The lighting device of claim 19 wherein the show packet further comprises information regarding a number of repeat packets associated with the data structure.

21. A lighting device comprising;
a light source;
a control circuit configured to control the operation of the light source; and
a communication device positioned in communication with the control circuit;
wherein the communication device is configured to receive a transmission having information relating to a lighting spectrum, a fade type, and a fade duration; and
wherein the control circuit is configured to operate the light source to emit light transitioning from a present light emission having a present spectral power distribution to a light emission having spectral power distribution indicated by the lighting spectrum according to the fade type and fade duration.

* * * * *